US006866783B2

(12) United States Patent
Baurmeister et al.

(10) Patent No.: US 6,866,783 B2
(45) Date of Patent: Mar. 15, 2005

(54) MODULE WITH MEMBRANE ELEMENTS IN CROSS-FLOW AND IN A DEAD-END ARRANGEMENT

(75) Inventors: Ulrich Baurmeister, Wuppertal (DE); Rudolf Wollbeck, Erlenbach (DE)

(73) Assignee: MAT Adsorption Technologies GmbH & Co. KG, Wuppertal (DE)

( * ) Notice: Subject to any disclaimer, the term of this patent is extended or adjusted under 35 U.S.C. 154(b) by 255 days.

(21) Appl. No.: 10/220,861

(22) PCT Filed: Feb. 26, 2001

(86) PCT No.: PCT/EP01/02147
§ 371 (c)(1),
(2), (4) Date: Nov. 12, 2002

(87) PCT Pub. No.: WO01/66237
PCT Pub. Date: Sep. 13, 2001

(65) Prior Publication Data
US 2003/0111414 A1 Jun. 19, 2003

(30) Foreign Application Priority Data
Mar. 7, 2000 (DE) .......................................... 100 11 014

(51) Int. Cl.$^7$ .............................................. B01D 63/00
(52) U.S. Cl. ............... 210/649; 210/500.23; 210/502.1; 210/641; 210/650; 210/321.74; 210/321.75
(58) Field of Search ................................. 210/649, 650, 210/641, 500.23, 502.1, 321.79, 321.8, 321.6, 321.72, 321.87, 321.81, 321.78, 638, 639, 321.74, 321.75; 96/8

(56) References Cited

U.S. PATENT DOCUMENTS

| | | | | |
|---|---|---|---|---|
| 4,266,026 A | * | 5/1981 | Breslau | 435/99 |
| 5,516,691 A | * | 5/1996 | Gerlach | 435/297.1 |
| 5,618,418 A | | 4/1997 | Demmer et al. | |
| 5,693,230 A | * | 12/1997 | Asher | 210/650 |
| 5,922,200 A | | 7/1999 | Pearl et al. | |
| 6,270,674 B1 | * | 8/2001 | Baurmeister et al. | 210/649 |

FOREIGN PATENT DOCUMENTS

| | | |
|---|---|---|
| DE | 33 02 384 A1 | 7/1984 |
| DE | 37 09 432 A1 | 10/1988 |

(List continued on next page.)

OTHER PUBLICATIONS

Brandt et al., "Membrane-based affinity technology for commercial scale purifications", Bio Technology, vol. 6, pp. 779–782, 1988.

(List continued on next page.)

Primary Examiner—W. L. Walker
Assistant Examiner—Krishnan S Menon
(74) Attorney, Agent, or Firm—Oliff & Berridge, PLC

(57) ABSTRACT

Membrane module for substance-specific treatment of fluids, such that the module has first and second membrane elements arranged with one end pointing toward a distribution space and the other end pointing toward a collection space. Each of the membrane elements have a cavity formed by a membrane wall. The first membrane elements have their ends embedded in sealing compounds such that their cavities open into the distribution space and collection space. The second membrane elements are also embedded in the sealing compound at the end pointing toward the collection space. The cavities of the second membrane elements open into the collection space, but are closed at the end pointing toward the distribution space. The fluid to be treated flows through the first membrane elements in cross-flow mode. In the process, part of the fluid passes through the membrane wall as a permeate, which then passes through the second membrane elements in dead-end mode. The retentate leaving the first membrane elements and the permeate conducted through the second membrane elements are combined within the membrane module and are removed from it as treated fluid. The substance-specific treatment is carried out on the permeate.

37 Claims, 6 Drawing Sheets

FOREIGN PATENT DOCUMENTS

| | | |
|---|---|---|
| DE | 39 23 128 A1 | 1/1991 |
| DE | 195 01 726 A1 | 7/1996 |
| DE | 196 45 537 A1 | 5/1998 |
| EP | 0 285 812 B1 | 10/1988 |
| EP | 0 341 413 A2 | 11/1989 |
| EP | 0 490 940 B1 | 6/1992 |
| EP | 0 787 523 A1 | 8/1997 |
| EP | 0 888 809 A1 | 1/1999 |
| WO | WO 90/05018 | 5/1990 |

OTHER PUBLICATIONS

Sakai, "Determination of pore size and pore size distribution 2. Dialysis membranes", J. Membrane Science, pp. 131–165.

Nakao, "Determination of pore size and pore size distribution 3. Filtaration membranes", J. Membrane Science, pp. 131–165, 1994.

Zeman et al., "Characterization of microfiltration membranes by image analysis of electron micrographs. Part 1. Method development", J. Membrane Science, pp. 221–231, 1992.

Kaneko, "Determination of pore size and pore size distribution 1. Adsorbents and catalysts", J. Membrane Science, pp. 59–89, 1994.

Muller, "New ion exchangers for the chromatography of biopolymers", Journal of Chromatography, 510, pp. 133–140, 1990.

Tsuneda et al., "Binding of Lysozyme onto a Cation–Exchange Microporous Membrane Containing Tentacle–Type Grafted Polymer Branches", Biotechnol. Prog., pp. 76–81, 1994.

Tsuneda et al., "High–throughput processing of proteins using a porous and tentacle anion–exchange membrane", Journal of Chromatography A pp. 211–218, 1995.

\* cited by examiner

MODULE WITH MEMBRANE ELEMENTS IN CROSS-FLOW AND IN A DEAD-END ARRANGEMENT

This application is a 371 of PCT/EP01/02147 of Feb. 26, 2001 and claims priority over the German Application 100 11 014.2 of Mar. 07, 2000.

BACKGROUND OF THE INVENTION

1. Field of the Invention

The invention relates to a membrane module for substance-specific treatment of a fluid, comprising a housing, an inlet arrangement for feeding the fluid to be treated into a distribution space in the housing, an outlet arrangement for removing the treated fluid from the housing via a collection space, and first membrane elements arranged in the housing and having a porous, semipermeable wall, each having one end pointing toward the distribution space and the other toward the collection space and a cavity formed by the wall, wherein the first membrane elements are embedded in a first sealing compound at the end pointing toward the distribution space and in a second sealing compound at the end pointing toward the collection space, such that the ends extend through the sealing compounds and each of the cavities of the first membrane elements is open at the end pointing toward the distribution space as well as at the end pointing toward the collection space and opens into the distribution space and collection space.

The invention also relates to a process for substance-specific treatment of a fluid.

2. Discussion of Related Art

Substance-specific treatments of fluids are becoming increasingly important in such application areas such as biotechnology, medicine, and chemical technology. Fluids in the context of the present invention are understood to include gases, gas mixtures, and liquids in general, such as protein solutions, suspensions or clear solutions. An example of a substance-specific treatment is the isolation of active agents from cell suspensions in which genetically modified cells have produced substances such as antibodies, hormones, growth factors, or enzymes, usually in small concentrations. Other important applications are the extracorporeal removal of undesired substances from human blood plasma and extraction of components such as immunoglobulins or clotting factors from the plasma of donated blood. Finally, another broad application area is the catalytic or biocatalytic—enzymatic—treatment of liquids, such as the hydrolysis of oils by lipases immobilized in a matrix.

The substance-specific treatment of fluids is frequently conducted such that the fluid to be treated is brought into contact with a carrier material, on and/or in which functional groups or substances are immobilized that, in a specific, selective manner, interact with the target substance contained in the fluid, i.e., with the substance that is the object of the substance-specific treatment. Such interactions can be, for example, cation or anion exchange, hydrophilic/hydrophobic interaction, hydrogen bridge formation, affinity, or enzymatic or catalytic reactions, and the like. In affinity separation of substances, such as affinity chromatography, ligands are coupled to or immobilized in the carrier material. The ligands have the function of adsorptively binding a specific single target substance or an entire class of substances. This target substance is termed a ligate. Examples of class-specific ligands are positively charged diethylaminoethyl (DEAE) groups or negatively charged sulfonic acid ($SO_3$) groups, which adsorb the class of positively or negatively charged molecules, respectively. Specific ligands are, for example, antibodies against a certain protein, which is bound as a ligate to the antibody.

Substance-specific treatments in the context of the present invention, however, are also understood to be those treatments by which molecules or particles are separated or retained due to their size. For a number of applications, it is desirable or necessary to subject a fluid to be treated to several, possibly different, substance-specific treatments. Thus, in the case of filtration processes of suspensions with differing particle fractions, it may be necessary to first prefilter larger particles with a coarse, open-pored prefilter and then to subject the filtrate to further substance-specific treatment, according to size or to affinity for a ligand, for example.

The primary criteria in the substance-specific treatment of fluids are productivity and selectivity. With a view toward productivity, it is important that, per unit of volume, as many functional groups as possible are available that can interact with the target substance contained in the fluid to be treated. At the same time, it is desirable to maximize the transport of the target substance to the functional groups or substances. In many such processes for substance-specific treatment of fluids, membranes with a porous structure are now used as carrier materials for functional groups. Due to their porous structure, membranes present a large inner surface area so that a large number of functional groups can be coupled to the membranes at a high concentration per unit volume. These functional groups interact with the fluids to be treated that pass through the membrane. (See, for example, E. Klein, "Affinity Membranes", John Wiley & Sons, Inc., 1991; S. Brandt et al., "Membrane-Based Affinity Technology for Commercial Scale Purifications," Bio/Technology Vol. 6 (1988), 779–782.)

Adaptation to the requirements of the treatment method can be attained via the type of the membrane used. Membranes are available in the form of hollow fibers or as flat membranes made from a wide variety of materials so that adaptation to the physicochemical properties of the fluids to be treated is possible. In addition, the pore size of the membranes can be adjusted such that a fluid to be treated, for example, containing a target substance, can pass through the membrane convectively, and, in the case of binding of the target substance to the interacting groups, there is no blockage of the membrane.

For a given linear flow rate, the thickness of the membrane wall can influence the residence time of the fluid to be treated in the membrane and the pressure drop during flow. Due to their generally thin walls (<300 $\mu$m, for example), membranes are distinguished by short transport distances for the fluid to be treated to interacting groups immobilized in the membranes, for example, resulting in relatively short residence times, low pressure drops, high linear flow rates, and therefore, high binding rates.

A number of devices containing such membranes have been described that are used in processes for substance-specific treatment of fluids. A distinction must be made here between the so-called dead-end mode or dead-end modules and cross-flow mode or cross-flow modules.

In cross-flow mode, the fluid to be treated flows as a feed stream parallel to one side of the membrane and a portion of the feed stream flows through the membrane as the permeate. It follows that in cross-flow modules only a part of the liquid to be treated, i.e., the part that passes through the membrane wall as a permeate, can undergo substance-specific treatment, which generally occurs in the membrane wall or possibly in the outer space of the membranes.

In dead-end mode, on the other hand, the entire fluid entering the membrane module as a feed stream is directed through the membrane and is removed as a filtrate or permeate from the downstream side of the membrane, which is opposite the inlet side.

WO 90/05018 discloses a cross-flow module with hollow-fiber membranes for use in affinity separation processes. In this module, a ligate-containing liquid is directed into the module housing via an inlet arrangement and flows tangentially over one side of the hollow-fiber membranes in and to which the ligands have been coupled. A portion of the liquid enters the membrane and flows through it, the ligates becoming attached to the ligands, and exits as a permeate stream on the side of the membrane opposite the inlet side. The retentate and permeate streams are removed via separate outlet arrangements.

In EP-A-0 341 413, an adsorber module is described for treatment of whole blood in which the hollow-fiber membranes, which are contained in the module embedded in sealing compounds at both ends and provided with ligands, are subjected to blood flow through the lumen in cross-flow mode. Plasma enters the outer space enclosing the hollow-fiber membranes as a permeate through the hollow-fiber membrane wall, the treatment of the plasma taking place in the membrane wall. In a specific embodiment, this module has no outlet for the permeate. Instead, the plasma separated as a permeate accumulates in the outer space surrounding the capillaries, and due to the developing pressure conditions, re-enters the lumen of the hollow-fiber membrane through the hollow-fiber membrane wall. In this module concept the permeate stream must pass through the membrane wall twice so that the flow through the membrane is almost zero over a large area. On the other hand, the flow is very high in the inlet region. A module of this type has the disadvantage that, in regions of high flow, the binding capacity is soon exhausted while the capacity in regions of low flow is not fully exploited.

DE-A-33 02 384 describes a dead-end module for blood plasma treatment containing hollow-fiber membranes. This module contains two adjacent hollow-fiber-membrane bundles, connected in series, for separation of pathological molecules from blood plasma by fractionation according to particle size. The ends of the hollow-fiber membranes of the two membrane bundles are embedded together in the module housing such that the hollow-fiber membranes of the first membrane bundle are open at the end toward the module inlet and closed at the other end, while the hollow-fiber membranes of the second membrane bundle are open at the end toward the module outlet and closed at the other end. The open ends of the two hollow-fiber bundles are therefore arranged oppositely. During operation, the blood plasma to be treated and from which the pathogenic components are to be filtered off, flows in dead-end mode initially via the open ends of the hollow-fiber membranes of the first membrane bundle into the lumen of these membranes and through their walls into the extraluminal region. Once filtered in this manner, the plasma then flows from the outside to the inside into the lumen of the hollow-fiber membranes of the second membrane bundle and leaves them through their open ends.

DE-A-37 09 432 discloses a dead-end module for sterilization of liquid media. This module contains two adjacent hollow-fiber-membrane bundles connected in series and is structurally similar to that described in DE-A-33 02 384. In the module of DE-A-37 09 432, the membrane of at least one of the hollow-fiber bundles can carry adsorptive material. In addition, the bundles may be surrounded by an additional filtration device that is in the form of a flexible, semipermeable tube and can also carry adsorptive material.

U.S. Pat. No. 5,693,230 also discloses a dead-end module with two groups of hollow-fiber membranes, wherein all the hollow-fiber membranes are open at one end and closed at the other. In this case, the module contains first hollow-fiber membranes for feeding in the fluid to be treated and second hollow-fiber membranes to remove the treated fluid. The fluid to be treated enters through the open ends of the first hollow-fiber membranes into their lumina, passes through the porous wall of these membranes into the outer space surrounding the first and second hollow-fiber membranes, and is directed from there through the porous wall of the second hollow-fiber membranes into their lumina and discharged through their open ends. In the outer space, the fluid is brought into contact with a treatment medium present there, and is treated.

In contrast to cross-flow modules, dead-end modules generally have the disadvantage that their applicability in the treatment of suspensions is very severely restricted, because in this design, the suspended particles are, as a rule, retained by the membrane used. Moreover, prior art dead-end membrane modules are less versatile in the sense that only a single substance-specific treatment can generally be carried out on a fluid to be treated.

It is therefore an object of the present invention to provide a membrane module of the type initially described in which the disadvantages of prior art membrane modules are reduced to at least some extent, and which is suitable for substance-specific treatment of both clear solutions and, in particular, suspensions, and can be flexibly adapted for the particular fluid treatment required, and, in particular, allows various types of substance-specific treatments to be carried out in direct succession.

It is furthermore an object of the present invention to provide a process for efficient substance-specific treatment of fluids using a module comprising semipermeable membranes of porous structure, which at least reduces the aforementioned disadvantages and allows, for example, improved utilization of the functional groups immobilized in the module and the substance-specific treatment of suspensions.

SUMMARY OF THE INVENTION

The object is achieved with a membrane module for substance-specific treatment of a fluid, in that the membrane module also comprises second membrane elements arranged in the housing and having a porous, semipermeable wall, one end pointing toward the distribution space and the other toward the collection space, and a cavity formed by the wall, wherein the second membrane elements, at the end pointing toward the collection space, are embedded along with the first membrane elements, in the second sealing compound such that these ends extend through the second sealing compound, and the cavities of the second membrane elements are open at this end and open into the collection space, and the second membrane elements are closed at the end pointing toward the distribution space, the first and second membrane elements forming a membrane-element arrangement and an outer space being formed between the sealing compounds that is partitioned in a fluid-tight manner from the distribution space and collection space and delimited by the sealing compounds, the inner wall of the housing, and the membrane elements.

The extent of the first and second membrane elements in the direction between the sealing compound pointing toward the distribution space and the sealing compound pointing toward the collection space is greater than the extent in at least one of the perpendicular directions.

Fluid-tight partitioning of the outer space from the distribution space and collection space is understood herein to mean that any fluid in the distribution space can pass into the outer space only via the first membrane elements and vice versa, and any fluid in the outer space can pass into the collection space only via the first or second membrane elements and vice versa.

In the application, the fluid to be treated is introduced as a feed stream into the membrane module of the invention and is directed in cross-flow mode along the side of the walls of the first membrane elements facing the cavity, such that part of the feed stream passes through the semipermeable walls of the first membrane elements as a permeate, and the remainder of the feed stream flows through the cavities of the first membrane elements as a retentate and finally exits from these at the end toward the collection space. After emerging from the walls of the first membrane elements, the permeate flows through the outer space essentially in the direction of the second membrane elements. At least a substantial proportion of the permeate passes in dead-end mode through the semipermeable walls of the second membrane elements and into their cavities, flows through these cavities, exits the second membrane elements at their open end, which point towards the collection space, and passes into the collection space. Here, it is combined with the retentate exiting from the first membrane elements. Between its separation from the feed stream and combination with the retentate, the permeate is subjected to at least one substance-specific treatment.

Depending on the embodiment of the membrane module of the invention, i.e., on the pressure conditions prevailing in the module, a portion of the permeate that has flowed into the outer space may, instead of passing through the second membrane elements, flow via back filtration in the region ahead of the sealing compound facing the collection space, through the walls of the first membrane elements and into their cavities to be combined there with the retentate. According to the invention, however, at least a substantial proportion of the permeate, and preferably at least 50% of the permeate, passes through the second membrane elements.

The fluid stream comprising the combined retentate and permeate leaves the housing via the outlet arrangement as a treated fluid. In the form of the first and second membrane elements, the membrane module of the invention integrates at least two different treatment stages connected in series, wherein the treatment stage involving flow in dead-end mode requires no separate pumps or governing apparatus. The partial streams leaving the treatment stages are recombined within the module and leave the membrane module of the invention as a single fluid stream.

The object is therefore furthermore achieved by a process for substance-specific treatment of a fluid, the process comprising at least the following steps:

a) introducing the fluid to be treated as a feed stream into a module containing at least one first membrane and at least one second membrane;

b) directing the feed stream in cross-flow mode along one side of the first membrane, such that part of the feed stream passes as a permeate through the first membrane and exits from the first membrane on its other side, while the remainder of the feed stream continues flowing along the first membrane as a retentate;

c) introducing at least a substantial portion of the permeate in dead-end mode to the second membrane on one side of this membrane, passing the permeate through the second membrane, and removing it from the second membrane on its other side;

d) combining the permeate and retentate within the module to yield the treated fluid; and e) removing the treated fluid from the module, wherein the permeate is subjected to at least one substance-specific treatment between its separation from the feed stream and its recombination with the retentate.

Due to the specific combination of membranes along the fluid flows in cross-flow mode with membranes through which the fluid flows in dead-end mode, the process of the invention can be advantageously used for treatment of suspensions. In a preferred embodiment, the process of the invention uses a membrane module of the invention.

BRIEF DESCRIPTION OF DRAWINGS

The invention will now be explained in more detail with reference to the figures, which are simplified schematic representations.

DESCRIPTION OF PREFERRED EMBODIMENTS

Figure 1:
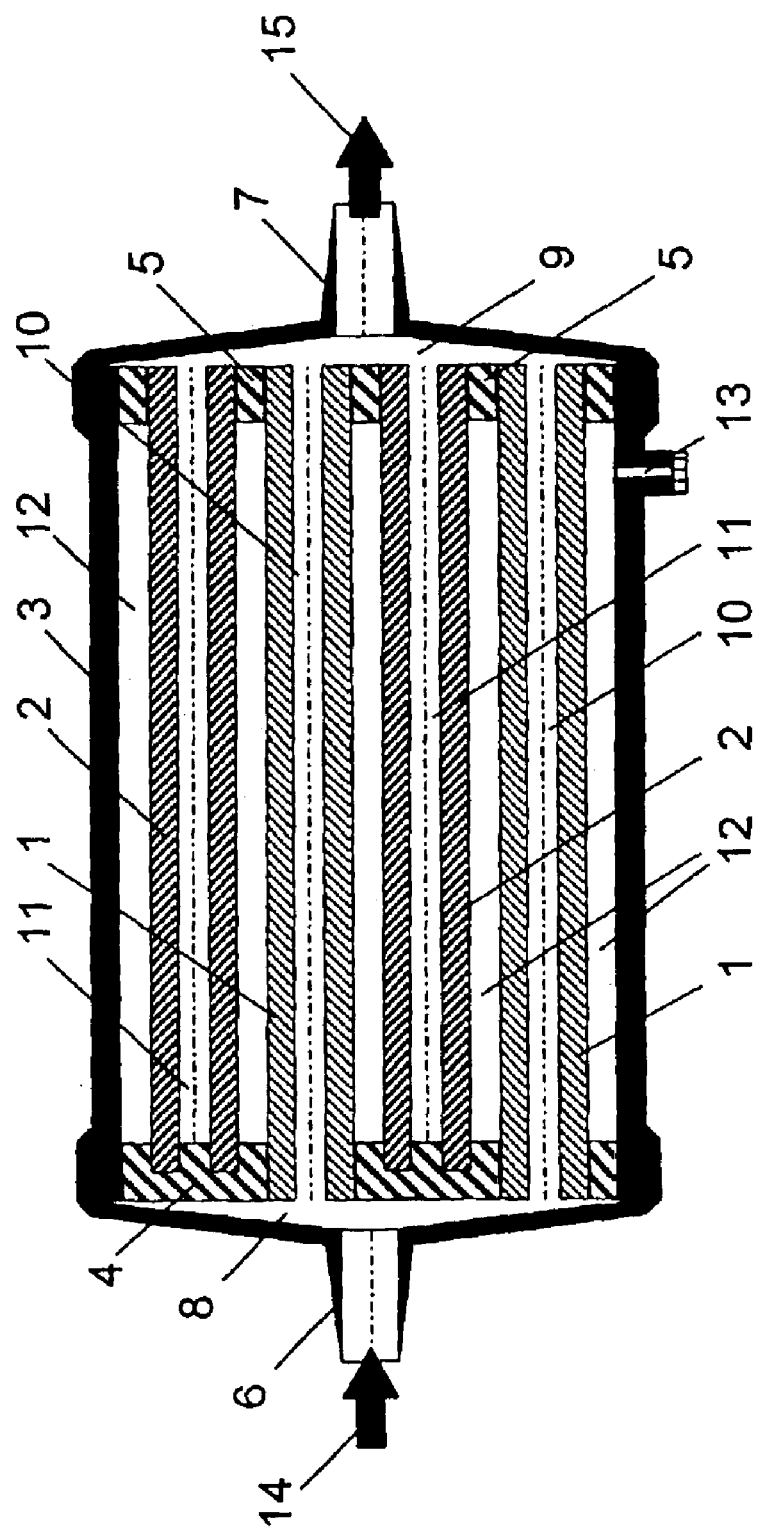
FIG. 1 is a membrane module with first and second membrane elements in the form of hollow-fiber membranes.

According to the invention, the first and second membrane elements are embedded at their open ends, which point toward the collection space, in the second sealing compound, adjacent to the collection space. These ends extend through this sealing compound so that an opening of the respective cavity to the collection space is provided. The open ends of the first membrane elements pointing toward the distribution space are, according to the invention, embedded in the first sealing compound adjacent to the distribution space in such a way that these ends extend through the sealing compound, so that an opening of the cavities of the first membrane elements is provided to the distribution space as well.

The materials normally used as sealing compounds for this purpose are, for example, epoxy resins, polyurethane resins, or hot-melt adhesives, which in the liquid state allow simple and fluid-tight embedding of the membrane elements. However, sealing compounds are understood to also include embodiments in which a sealing compound is first prefabricated, for example, as an injection-molded part provided with appropriate recesses for acceptance of the membrane elements, into which the membrane elements may be secured in a fluid-tight manner, such as by means of an adhesive.

The closed ends of the second membrane elements may end in the outer space surrounding the membrane elements, i.e., without being embedded. Alternatively, they may be embedded, along with those ends of the first membrane elements pointing toward the distribution space, in the first sealing compound adjacent to the distribution space but in such a manner that the ends of the second membrane elements pointing toward the distribution space remain closed.

In a preferred embodiment of the membrane module of the invention, the membrane-element arrangement is made from sheet-form layers. This allows the attainment of a high degree of order and a well defined flow between the first and second membrane elements. This applies particularly if first and second membrane elements are directly adjacent to one another, and are arranged, for example, in an alternating sequence. A particularly preferred structure of the membrane-element arrangement is one in which sheet-form layers of membrane elements are superimposed to form a stack. Another especially preferred embodiment the membrane-element arrangement comprises sheet-form layers wound spirally about a winding axis. In the context of the present invention, a sheet-form layer is understood to be a layer whose dimensions in the planar state (i.e., before spiral winding, for example) in the longitudinal direction of the membrane elements between their ends and in one direction perpendicular thereto, are appreciably greater than in the direction of the other perpendicular to the membrane elements, which determines the thickness of the layer.

The membrane-element arrangement preferably comprises first and second layers, wherein the first layers comprising only first membrane elements and the second layers only comprises second membrane elements. An arrangement comprising an alternating sequence of first and second layers is especially preferred.

In a preferred embodiment of the invention, the first and second membrane elements are hollow-fiber membranes and the cavities of the membrane elements are formed by the lumina of the hollow-fiber membranes. In the preferred embodiment wherein the structure comprises a membrane-element arrangement in sheet-form layers, the hollow-fiber membranes within the layers are arranged essentially parallel to one another. The hollow-fiber membranes are embedded in the membrane-module housing in such a way that the lumina of the first hollow-fiber membranes functioning as first membrane elements are open at both ends, and the lumina of the second hollow-fiber membranes functioning as second membrane elements are open only at the end pointing toward the collection space and closed at the end pointing toward the distribution space. The closure at the closed end of the second hollow-fiber membranes can be effected by, for example, the sealing compound or by heat sealing. In a preferred embodiment, the second membrane elements are formed by bending or folding hollow fibers of the appropriate length into a U-shape, or arranging them in the form of a loop, so as to yield two interconnected second membrane elements whose cavities are closed in the direction of the distribution space and open in the direction of the collection space.

In place of hollow-fiber membranes, membrane tubes or membrane pipes may be used, which have generally larger diameters and wall thicknesses than the hollow-fiber membranes.

Hollow-fiber membranes with differing outer contours, i.e., differing outlines when viewed in cross-section, can be used. The hollow-fiber membranes can, for example, have a contour that is essentially round or circular, triangular, rectangular, hexagonal, or octagonal. They can also be oval, elliptical, or with three or four lobes, etc. For use in the membrane module of the invention, hollow-fiber membranes have proven satisfactory that have a wall thickness between about 15 $\mu$m and about 900 $\mu$m, and hollow-fiber membranes with a wall thickness between about 30 $\mu$m and about 100 $\mu$m for the first membrane elements and between about 100 $\mu$m and about 300 $\mu$m for the second membrane elements have proven especially satisfactory.

Preferably, the hydraulic diameter of the lumen of the hollow-fiber membranes employed is about 50 $\mu$m to about 1,500 $\mu$m, and hollow-fiber membranes with a hydraulic diameter of the lumen between about 80 $\mu$m and about 300 $\mu$m are especially preferred. The hydraulic diameter is defined as $4*A/U$, wherein A is the area of the flow cross-section of the hollow-fiber lumen and U is the circumference of the flow cross-section of the respective hollow-fiber lumen. For certain applications, and especially where the functions of the first and second membrane elements are different, the hydraulic diameters of the hollow-fiber membranes employed as first and second membrane elements can be chosen so as to be different.

The first and second hollow-fiber membranes are preferably bound in each case into at least one. hollow-fiber mat, wherein the hollow-fiber membranes within a mat are arranged essentially parallel to one another. In these hollow-fiber mats, the hollow-fiber membranes are preferably bound by means of textile threads. Using known methods, such mats can advantageously be produced as knitted or woven mats, but also as small woven ribbons or crocheted mats. In the case of wovens or knits, the textile threads are the warp threads running transversely to the hollow-fiber membranes. These transverse threads hold the hollow-fiber membranes essentially parallel to one another. Such hollow-fiber mats provide an easy means of implementing a structure with a membrane-element arrangement of sheet-form layers.

In a preferred embodiment, a hollow-fiber mat of this type contains both first and second hollow-fiber membranes. Depending on what is required of the membrane module of the invention, the first and second hollow-fiber membranes within such mats can be arranged in alternating sequence or can be present in unequal numbers, in which case the first hollow-fiber membranes and the second hollow-fiber membranes may also be combined into groups.

Hollow-fiber mats with an alternating sequence of first and second hollow-fiber membranes can be produced, for example, by knitting together hollow-fiber membranes fed into a Raschel machine alternately and in parallel as weft threads. In this process, the first hollow-fiber membranes are distinguished from the second before their joint embedding in the sealing compound because, for example, the first hollow-fiber membranes are closed, for example, by meander-form placement at both ends of the mat, whereas the second hollow-fiber membranes within a mat are open at one edge of the mat. The open side, when embedded in a sealing compound, is closed by the sealing compound. On the other hand, no sealing compound can penetrate into the previously closed ends during embedding, so that when the sealing compound is subsequently cut through, the originally closed lumina of the hollow-fiber membranes on this side are opened.

A mat of this type can also be produced, for example, on a Raschel machine with meander-form placement of the hollow fibers as weft threads, such that the loops of the second hollow-fiber membranes at one edge of the mat are displaced inward from the edge of the mat to such an extent that the cut following the embedding in the sealing compound does not affect the second capillary membranes on this side and thus the closed side of the second membrane elements is produced. The remaining loops of the first and second membrane elements are formed during Raschel knitting such that they are cut off after the embedding in the sealing compound, so that the lumina of all the hollow-fiber membranes on this side are opened.

Different area and weight relationships within a mat can be obtained by varying the numbers of alternating first and second hollow-fiber membranes. When incorporating first and second hollow-fiber membranes into the same hollow-fiber mat, it is advantageous if the first and second hollow-fiber membranes are of at least very nearly the same outside diameter.

In another preferred embodiment, each hollow-fiber mat comprises only first hollow-fiber membranes or only second hollow-fiber membranes. Mats with first hollow-fiber membranes can be produced, for example, from meander-form woven or knitted hollow-fiber membrane mats at whose side edges the hollow-fiber membranes form an arch, and for this reason, are initially closed at these edges. After the embedding, the hollow-fiber membranes can be opened on both sides by cutting off the end arches at both sides of the mat while trimming the respective sealing compound. Mats with second hollow-fiber membranes can also be produced from such meander-form woven or knitted hollow-fiber membrane mats by cutting off the end arches at only one of the two edges so that the hollow-fiber membranes are opened on one side. Preferably, however, a mat with second hollow-fiber membranes is produced by dividing a meander-form woven or knitted mat down the middle so that two halves are produced, each with hollow-fiber membranes whose cavities are open on one side.

In a further embodiment of the invention, the hollow-fiber membranes are incorporated into the respective hollow-fiber mat by means of flat connecting elements, preferably in the form of strips. These strip-like connecting elements may run perpendicular, or at some other angle, to the mutually parallel hollow-fiber membranes and may be laminated onto these by means of pointwise application of an adhesive, which, for example, can be polyurethane based.

In an advantageous embodiment, a number of hollow-fiber mats are stacked on top of one another such that the hollow-fiber mats form planar sheet-form layers. In a further preferred embodiment of the apparatus of the invention, at least one hollow-fiber mat comprising first and second hollow-fiber membranes is folded zigzag fashion to form a stack. In a further preferred embodiment, at least one hollow-fiber mat comprising only first hollow-fiber membranes and at least one hollow-fiber mat comprising only second hollow-fiber membranes are superimposed and folded together zigzag fashion into a stack. In a likewise advantageous embodiment, at least one hollow-fiber mat comprising first and second hollow-fiber membranes is wound spirally about a winding axis parallel to the hollow-fiber membranes to give a structure comprising sheet-form layers. When using hollow-fiber mats comprising only first or only; second hollow-fiber membranes, at least one hollow-fiber mat comprising only first hollow-fiber membranes and at least one comprising only second hollow-fiber membranes are superimposed and wound together spirally about a winding axis parallel to the hollow-fiber membranes. The winding axis could also be, for example, a winding core of which the cross-section and structure can be freely selected. The winding core should preferably be removable so that it can be withdrawn after winding without leaving an appreciable gap in the bundle produced by the winding.

In a preferred embodiment of the membrane module of the invention, the hollow-fiber membranes within the sheet-form layers are essentially parallel to those in adjacent layers. Depending on the application of the membrane modules of the invention, however, defined spaces can also exist between the hollow-fiber membranes, i.e., if a defined configuration of the outer space is required. An advantageous membrane-element arrangement in these cases is one produced by spiral winding of at least two superimposed hollow-fiber mats about an axis or core, the hollow-fiber membranes within each mat being spaced from each other and the hollow-fiber mats being superimposed such that the hollow fibers of the superimposed hollow-fiber mats cross at an angle. The manufacture of bundles of this type has been described in detail in EP-A-0 285 812. For such bundles, the angle between the crossing hollow-fiber membranes can be between about 0° and about 120°, with angles between about 30° and about 90° having proven advantageous.

In another preferred embodiment of the membrane module of the invention, the first membrane elements are hollow-fiber membranes and the second membrane elements are each formed from at least one flat membrane. An advantageous embodiment of such a second membrane element comprising at least one flat membrane can be produced from an essentially rectangular or square section of a flat membrane folded into a U-shape, wherein, in addition to the fold edge, two other side edges, for example, the side edges perpendicular to the fold edge are sealed off by heat or adhesive, for example. The two flanks formed by the U-shaped folding of such a section of a flat membrane are separated by spacers and thus, together with the closed fold edge and the closed side edges, form a cavity open on one side. The open side-edge in the membrane module of the invention points toward the collection space.

According to another advantageous embodiment of the invention, such second membrane elements comprising at least one flat membrane are each made of two equal-sized flat membranes, essentially parallel to each other and essentially rectangular or square, arranged such that their edges run parallel to each other, the flat membranes being spaced from one another by spacers. The two flat membranes are positively joined to each other at three edges, for example, by heat sealing or adhesive, that is, at the edge pointing toward the distribution space and the edges perpendicular to this edge, so that the flanks of the membrane element are formed by the flat membranes. The cavity in turn is formed by the flanks and the positively joined edges. The remaining, open, side edge points in the direction of the collection space.

The two flat-membrane sections used can be identical, or they can be different with respect to, for example, their material, their structure, or the functional groups provided for interacting with target substances. One of the two flat membranes can also be replaced by a fluid-impermeable film, for example, where this is deemed desirable for reasons of stability of the membrane elements or for production considerations.

The flat-membrane elements described are arranged in the membrane module of the invention such that the remaining open side edge points toward the collection space and the cavity is open to this space.

The spacers, which, as mentioned above, ensure a defined spacing between the flanks of the treatment elements made from flat membranes and should also be fluid-permeable, can exist as separate elements. The spacers used can be a fluid-permeable material such as a nonwoven or woven fabric. The spacer function on the inside of the membrane can also be integrated into the membrane or film itself, however, such as by surface structures with grooved, nubbed, or other profiles.

The flat membranes used in the apparatus of the invention or to conduct the process of the invention preferably have a wall thickness between about 15 $\mu$m and about 500 $\mu$m, a flat-membrane wall thickness between about 100 $\mu$m and about 300 $\mu$m being especially preferred.

Second membrane elements produced from flat membranes in this manner can be used in planar form and stacked along with first hollow fibers which are preferably bound into hollow-fiber mats. The stacks then comprise first planar sheet-form layers comprising the hollow-fiber membrane elements and second planar sheet-form layers comprising the flat-membrane elements. Zigzag folding together with hollow-fiber mats comprising first hollow-fiber membranes can also be advantageously implemented. In addition, the second membrane elements made up of flat membranes can also be wound spirally, together with first membrane elements in the form of hollow-fiber membranes, about a winding axis parallel to the hollow-fiber membranes and perpendicular to the open edge of the second membrane elements. In this case as well, the hollow-fiber membranes make up the first layers and the flat membranes the second layers. In the aforementioned arrangements, the second layers in each case can also comprise a single flat-membrane element.

While passing through the walls of the first membrane elements, through the outer space, and/or through the second membrane elements, the part of the fluid to be treated that has separated as the permeate stream is subjected to substance-specific treatment. For passage through the walls of the first membrane elements and/or through the second membrane elements, the only substance-specific treatment can be a fractionation of the substances contained in the fluid on the basis of their size, wherein such substances being present in the form of molecules or particles, for example. Preferably, however, the housing of the membrane module of the invention comprises a matrix on and/or in which functional groups are immobilized that, in a specific, selective manner, interact with a single target substance or several target substances contained in the fluid to be treated, i.e., with the substances that are the object of the substance-specific treatment.

In a preferred embodiment of the invention, the first membrane elements and/or second membrane elements are the matrix for the functional groups, and the functional groups are immobilized on and/or in the membrane elements. In this case, it is especially preferable for both the first and second membrane elements to serve as the matrix for functional groups. However, the functional groups can be immobilized exclusively on and/or in the first, or exclusively on and/or in the second, membrane elements. Where both the first and second membrane elements serve as a matrix for functional groups, the functional groups in the respective membrane elements may be the same or different.

In a likewise preferred embodiment of the apparatus of the invention, carrier materials that are fluid-permeable, i.e., permeable to the fluid to be treated, are introduced between the first and second membrane elements. These carrier materials are the matrix for the functional groups, i.e., functional groups are immobilized on and/or in these carrier materials, which function as a matrix.

The carrier materials are preferably particles, it being advantageous for the preferred layered structure of the arrangement of first and second membranes if the particles are incorporated in a fluid-permeable nonwoven, a flat membrane, or the like. In the context of the present invention, particles are understood to include, for example, cells that interact in a specific manner with target substances directed toward them.

Likewise preferred carrier materials are semipermeable, porous flat membranes, which may also be single-layered or multilayered. The carrier materials may also be in the form of textile flat structures or likewise comprise hollow-fiber membrane mats, in which, however, the hollow-fiber membranes are closed at both ends, such as by embedding. In particular, those of the aforementioned carrier materials that are themselves in sheet form or layered are excellently suited for use in combination with the preferred layered structure of the arrangement of first and second membrane elements. It is practical in this case to embed these flat carrier materials in the sealing compounds along with the first and second membrane elements. Particularly in the case where a flat membrane is employed as a carrier material, a further treatment stage, operating in dead-end mode, can thereby be inserted between first and second membrane elements so that the cross-flow filtration in the first membrane elements is followed by two-fold dead-end filtration. In this case, the flat membrane used as a carrier material can also exercise a fractionating function in addition to serving to interact with target substances.

It is of course also possible to insert flat membranes in similar fashion between the first and second membrane elements as dead-end filters, wherein these flat membranes do not function as a carrier material for a matrix, but solely as a dead-end filtration stage, and serve to fractionate on the basis of particle size.

In the preferred case that only the carrier material is the matrix, the fluid to be treated flows out of the distribution space through the cavities of the first membrane elements, a partial stream passing through the walls of the first membrane elements as a permeate and, after leaving these walls, being distributed over the entire matrix, i.e., the entire carrier material, through which it then passes. During this process, the fluid is treated in a substance-specific manner. The treated fluid then enters through the walls of the adjacent second membrane elements into the cavities of these second membrane elements and flows out of these cavities into the adjacent collection space. Here, the substance-specifically treated permeate stream is combined with the retentate stream flowing out from the cavities of the first membrane elements to yield the substance-specifically treated fluid, which is then conducted out of the housing via the outlet arrangement.

The function of the first membrane elements can be restricted here purely to that of a distributor by means of which the fluid to be treated is advantageously and uniformly distributed over the entire carrier material, and the function of the second membrane elements to that of a collector by means of which the treated permeate is uniformly removed from the entire carrier material. In this way, a uniform usage of all the functional groups immobilized on and/or in the carrier material is achieved.

However, the first membrane elements can also simultaneously effect a substance-specific treatment in the form of a fractionation, so that, for example, only molecules or particles below a specific size can pass through the first membrane elements and be further transported for substance-specific treatment in the carrier material, while larger particles are retained and excluded from substance-specific treatment in the carrier material. Similarly the second membrane elements, in addition to their collection function, can also serve to retain, on the basis of particle size, for example, particulate components enclosed in the outer space and serving as a matrix.

In another advantageous embodiment of the apparatus of the invention, the first and second membrane elements, as well as the carrier materials, serve as a matrix for the functional groups. In this case, therefore, the first and second membrane elements serve as substance-specific treatment elements in addition to their distribution and collection functions. The functional groups immobilized in the membrane elements and the carrier material may be the same or different. In an advantageous embodiment of the process of the invention, the fluid to be treated is subjected consecutively to at least two different substance-specific treatments while flowing through the matrix, i.e., through the first and second membrane elements and the carrier material. It is of course also possible that, in addition to the carrier material, only the first or second membrane elements are a matrix for the substance-specific groups.

To increase the efficiency of the substance-specific treatment, it is of advantage for steps b) to d) of the process of the invention to be conducted multiple times, and especially advantageous for steps b) to d) to be conducted multiple times within the same membrane module. In a preferred embodiment of the membrane module of the invention, therefore, multiple (e.g., up to about 100) membrane-element arrangements are arranged sequentially as module stages in the housing between the inlet and outlet arrangements, i.e., in the direction of flow through the housing. By sequentially arranging a plurality of module stages, the dimension of an individual module stage in the direction of the flow through the housing can at the same time be kept short so that a change in concentration in regard to possible critical components in the fluid to be treated is kept low. This is especially important in processes for substance-specific treatment of suspensions where at least some of the suspended particles should be retained by the semipermeable membrane wall of, for example, the first membrane elements, while an excessive build-up of suspended particles should be avoided as, for example, in the substance-specific treatment of blood. If relatively short arrangements of membrane elements are used, only a small partial stream is removed from the fluid to be treated along the first membrane elements, so that concentration changes remain low until the subsequent merging of the retentate and permeate streams.

Preferably, up to about 10 module stages are arranged sequentially in the housing of the membrane module of the invention. A number of module stages up to about 3 has proven especially satisfactory. It is advantageous in this case if the individual module stages are spaced from one another to allow thorough mixing of the retentate and permeate streams in the respective collection spaces. Thorough mixing is advantageous, for example, to avoid undesired concentration fluctuations.

It is of course also possible, in adapting to the requirements of the treatment process, to sequentially arrange a plurality of membrane modules of the invention, which preferably comprise a plurality of module stages. It may also be practical to integrate the module of the invention with other modules, such as those for dialysis, hemodiafiltration, hemofiltration, heat exchange, or other process steps, depending on the application. In another preferred embodiment of the process of the invention, at least part of the treated fluid is recirculated, i.e., the treated fluid leaving the membrane module is again fed into the module as a feed stream, i.e., as fluid to be treated. The fluid therefore passes through the substance-specific treatment process multiple times so that the residence time of the fluid can be increased and the desired treatment level set.

In the case where substance-specific treatment occurs by functional groups beingimmobilized on and/or in a matrix, the fluid to be treated transports the target substance(s), preferably convectively, through the matrix. This requires that the first membrane elements, the second membrane elements, and/or the carrier material, which may be, for example, in the form of a semipermeable flat membrane of porous structure, have a pore size that permits convective transport of the fluid to be treated, including the target substance(s). In the application, the pore size must also be adapted to the size of the target substance(s), which can be present in the form of dissolved molecules or macromolecules or also as small particles with a size in the submicrometer range, in order to prevent retention of the target substance(s) due to their size.

On the other hand, in the light of the use of the membrane module of the invention, especially where membrane elements or a flat membrane serve as the matrix, it is important to use membranes with minimum pore sizes and maximum pore volume or porosity in order to provide maximum membrane inner surface area for the substance-specific treatment. Preferably, the membranes used in accordance with the invention have a mean porosity between about 50% and about 90% by volume. The mean porosity is understood to be the, ratio of the pore volume of the membrane to the membrane-wall volume, wherein the membrane-wall volume is the sum of the pore volume and the volume of the material constituting the membrane structure. Finally, in embodiments of the apparatus of the invention that comprise carrier materials in the form of particles, the pore size of the membrane elements must be adapted to the size of the particles such that the particles are retained by the membrane elements. In these cases, therefore, it is advantageous that the membranes be essentially permeable for the target substance(s) and essentially impermeable for the particles of the carrier material. The first and second membrane elements in this case can also have different pore sizes, especially if the direction of flow in the apparatus of the invention is always the same.

The requirements placed on the construction of the membranes, i.e., on their structure and pore size distribution across the membrane thickness, are given by the respective application for the substance-specific treatment. The membrane structure can be isotropic across the thickness, i.e., the pore diameters are essentially constant within the membrane structure, but it can also be anisotropic, symmetric, or even asymmetric. In the present context, an essentially isotropic pore structure is understood to be a structure in which the pore size in the directions of the extent of the membranes varies by a factor of about 10 at most. Such essentially isotropic structures are distinguished by their large inner surface area on which a large number of substance-specific groups can be immobilized. Furthermore, a structure of this type leads in the application to a uniform utilization of these groups. Membranes of isotropic structure are therefore preferred for embodiments of the membrane module of the invention in which the membranes employed are a matrix for the functional groups.

In the case where the first membrane elements perform a fractionating function and the second membrane elements serve as a matrix for functional groups, membranes of asymmetric structure, which have high hydraulic permeability along with high separation selectivity for the particulate components to be separated from the fluid, are preferably employed for the first membrane elements, and membranes of essentially isotropic pore structure for the second membrane elements.

The membranes used in the membrane module of the invention or to conduct the process of the invention preferably have a mean pore diameter between about 0.01 $\mu$m and about 10 $\mu$m. In the case of a membrane performing a fractionating function, the pore size of the separating layer depends on the size of the particulate components to be separated. The mean pore diameter in the separating layer of these membranes is generally between about 0.01 $\mu$m and about 1 $\mu$m and that in the underlying support structure between about 0.2 $\mu$m and about 10 $\mu$m. In those cases where the membrane is a matrix for functional groups, the preferred mean pore diameter is between about 0.2 $\mu$m and about 10 $\mu$m.

To determine the mean pore diameter, different methods are used depending on the pore diameter and membrane structure. For pore structures that are essentially isotropic, pore diameters are determined indirectly by a filtration experiment in which an aqueous dextran solution with a known size distribution of dextran molecules is filtered through the membrane. From the measured relative retention as a function of the nominal molecular diameter, the pore diameter distribution is calculated and from it the mean pore diameter. This method is described in, for example, K. Sakai in J. Membrane Science 96 (1994), pp. 91–130, and by Shin-ichi Nakao in J. Membrane Science 96 (1994), pp. 131–165, for dialysis and filtration membranes, respectively.

For anisotropic membranes that have a layer with denser pore structure, for example, the cited determination methods based on filtration experiments are also used to determine the mean pore diameter within the denser layer. To determine the mean pore diameter of the coarser-pore areas of the anisotropic membranes, an image-analysis method according to L. Zeman et al., J. Membrane Science 71 (1992), pp. 221–231, is employed. This method is suitable for pore sizes between 0.1 $\mu$m and 10 $\mu$m by its nature for both isotropic and anisotropic pore structures.

In cases where the first and/or second membrane elements and/or possibly the membranes used as a carrier medium are a matrix for functional groups, porous membranes with a large inner surface area are preferably used as a matrix in the apparatus of the invention or to conduct the process of the invention. Porous membranes have proven satisfactory that have a BET surface area between about 2 and about 300 $m^2$ per $cm^3$ of membrane volume, and those membranes with a BET surface area between about 4 and about 30 $m^2$ per $cm^3$ of membrane volume have proven especially satisfactory. The BET method for determining the surface area of porous membrane structures, which is based on the measurement of nitrogen adsorption, is described in K. Kaneko, J. Membrane Science 96 (1994), pp. 59–89.

Depending on the desired application of the apparatus or process of the invention, the membranes used for the first and second membrane elements, and any membranes used as a carrier material, can be the same or different. The differences can be with respect to their pore structure or pore diameter, for example, but also with respect to the functional groups contained in the membranes that are intended; for interaction with the target substances contained in the fluid to be treated.

If particles are used as carrier materials, it is practical to incorporate these, as described above, into, for example, a fluid-permeable nonwoven, a flat membrane, or the like, for example, to stabilize the position of the particles between the first and second membrane elements, or in the preferred case that the arrangement of first and second membrane elements has a layered construction, to achieve a uniform distribution of particles between the layers or also a uniform distance between the layers. The fluid-permeable nonwoven or, for example, flat membrane can have a relatively coarse structure. What is important is that the particles should be easily incorporated into the nonwoven or flat membrane and stably positioned there in subsequent use.

Particles of this kind can be, for example, those used in accordance with the prior art in columns for affinity chromatography. The structure of these particles can be dense so that the target substances contained in the fluid to be treated can be reached only via a dissolution process, for example, or by diffusion towards substance-specific functional groups immobilized in the interior of the particles. Preferably, however, the particles have a porous structure, and convective transport of the target substances to the immobilized, substance-specific groups, even to those on the inner surface defined by the pores, is possible. The pore diameter of these particles is preferably in the range between about 0.01 $\mu$m and about 10 $\mu$m and more preferably between about 0.1 $\mu$m and about 3 $\mu$m.

However, particles are also understood to include macromolecules such as proteins (for example, albumin), to which, for example, smaller molecules, such as bilirubin, may be bound, or, as stated above, cells. The particles can be spherical in shape or of any other form, for example, ellipsoidal or rod-shaped.

To introduce the particles, for example, or to deaerate the outer space around the membrane elements, it is practical to provide the membrane module of the invention with one or more sealable outlet and inlet openings in the housing wall.

There are no restrictions whatsoever with respect to the material from which the membrane elements, and, where applicable, the flat membranes used as a carrier material in accordance with the invention are made. Membranes can be used that are made from inorganic materials such as glass, ceramics, $SiO_2$, carbon, or metal, or from organic polymers or blends thereof. The polymers can be hydrophilic and/or hydrophobic in nature. They can be selected from the group of cellulosic polymers such as cellulose or regenerated cellulose, modified cellulose such as cellulose esters, cellulose: ethers, amine-modified celluloses, or blends of cellulosic polymers, from the group of synthetic polymers such as polyacrylonitrile and corresponding copolymers, polymers containing polyurethane, polyarylsulfones and polyarylethersulfones such as polysulfone or polyethersulfone, polyvinylidene fluoride, polytetrafluoroethylene, water-insoluble polyvinyl alcohols, aliphatic and aromatic polyamides, polyimides, polyetherimides, polyesters, polycarbonates, polyolefins such as polyethylene, polypropylene, polyvinyl chloride, polyphenylene oxide, polybenzimidazoles, and polybenzimidazolones, as well as from modifications, blends, mixtures, or copolymers derived from these polymers. Other polymers can be mixed as additives with these polymers or polymer blends, for example, polyethylene oxide, polyhydroxyether, polyethylene glycol, polyvinylpyrrolidone, polyvinyl alcohol, or polycaprolactone, or inorganic su substances such as $SiO_2$. In individual cases, the membrane can also have been subjected to a surface modification, for example, in order to establish certain properties of the membrane surface such as in the form of certain functional groups. Where polyolefinic polymers are used, it may be necessary to coat at least the inner surface of the membrane with a functionalizable polymer, for example.

There has been particularly good experience with membranes made from cellulosic polymers, polyamides, polypropylene, or polyethersulfones, or from solvent-stable and pH-stable polymers, in particular with membranes made from polytetrafluoroethylene or polyvinylidene fluoride, and from modifications, blends, mixtures, or copolymers derived therefrom. Such membranes are described in DE-A-39 23 128, for example.

The membrane module of the invention and the process of the invention can be successfully used in a wide variety of substance-specific treatments of fluids. In membrane modules containing a matrix, multiple different functional groups, depending on the respective treatment processes, can also be immobilized on and/or in the matrix. These interact specifically with various target substances. Different membranes with different substance-specific groups can also be used together, if the application requires this, for the first and second membrane elements and, if applicable, for the flat membrane used as a carrier material. In this way, different substance-specific treatments can be carried out in the matrix. In other cases, this treatment of the fluid via interaction with functional groups can be combined with a prefiltration of the fluid which then takes place in the first membrane elements in order, for example, to remove certain components from the fluid to be treated that are not to come into contact with the functional groups. When membrane modules with multiple module stages are used, the functional groups immobilized in the individual module stages may be the same or different.

For immobilization of functional groups on and/or in the matrix, the processes described in the literature can be employed. The functional groups that can be used for the respective types of substance-specific fluid treatment have also been described in the literature. Various possibilities for immobilization of the functional groups can be considered, with respect to both the location and manner in which they are immobilized.

These functional groups can be coupled to the matrix by adsorption or via covalent bonds. This coupling to the matrix can take place prior to insertion into the housing or after inserting the matrix into the housing of the membrane module of the invention. Depending on the individual application, the functional groups can, for example, be coupled essentially homogeneously to the entire surface of the matrix, i.e., to both the outer surface and the inner surface such as that formed by the pores, and thus be immobilized on and in the matrix. However, it can be necessary for the functional groups to be immobilized on only a portion of these surfaces, such as when individual components of the fluid to be treated should not come into contact with the functional groups.

There can also be a direct inclusion of functional groups in the matrix material, in the case of matrices made from polymeric materials by, for example, modification of the polymeric material with ionic, hydrophilic, or hydrophobic groups, for example, or by using polymer blends in which at least one polymer component has functional, i.e., substance-specific, groups.

Another possibility is to incorporate functional groups of this type, or carrier substances or particles having such groups, into the pore system of a membrane during its manufacture or, for example, to flood them into the finished membrane at a later stage. In the latter case, it is practical for the membrane to have an asymmetric structure and possibly a skin, wherein the openings of the skin or the pores of the fine-pored side of the membrane are dimensioned such that the functional groups or the cited carrier substances or particles cannot penetrate.

The pore size of the membrane used should preferably be selected such that the target substances can be transported convectively through the membrane wall by at least part of the fluid to be treated, despite the functional groups immobilized in the pores.

In accordance with an especially preferred embodiment of the invention, the functional groups are ligands for affinity separation of ligates from liquids to be treated, or catalysts, wherein catalysts are understood to include biocatalysts such as enzymes. Preferred processes of the invention are those for cleaning/separation of ligates from a ligate-containing liquid, wherein a matrix is selected on and/or in which ligands for these ligates are immobilized, or wherein membrane modules of the invention that contain such matrices are used. Other preferred processes are those for catalytic treatment of liquids, wherein a matrix is selected on and/or in which catalysts are immobilized, or wherein membrane modules of the invention that comprise such matrices are used. The catalytic processes also include biocatalytic processes such as enzyme processes.

As used herein, ligands can act non-specifically, group-specifically, or specifically. For details of the ligands that can be used, and the possibilities of their immobilization, the reader is referred to the European patent application EP-A-0 787 523, the relevant disclosures of which are expressly included herein as references.

Without providing an exhaustive list of possibilities at this point, the ligands can be produced, for example, by surface modification of the matrix bound to the surface directly or via spacer molecules, or bound to the surface via tentacle systems or chains, wherein a plurality of ligands can be bound to each chain or each tentacle system.

To increase the capacity of ion-exchange matrices in particular, there are various methods known per se that can be used to increase the number of substance-specific groups, i.e., ligands, on the surface of the matrices. Preferably, the ligands are coupled to the membrane via molecules of long-chain linear polymers, the molecules of the long-chain linear polymers carrying a plurality of ligands. The use of long-chain linear polymers with side arms, so-called tentacles, where the ligands are present on the tentacles is described in, for example, W. Müller in J. Chromatogr., Vol. 510 (1990), p. 133. The production of such tentacles is described in, for example, Tsuneda et al. (Biotechnol. Prog., Vol. 10 (1994), pp. 76–81, and J. Chromatogr., Vol. A 689 (1995), pp. 211–218), and can take place via radiation-induced graft polymerization of a monomer containing an epoxy group, such as glycidyl methacrylate, with subsequent chemical conversion into $SO_3H$ groups or diethylamino groups. Another method for grafting of nitrogenous polymeric flat membranes that can be used to increase the ion-exchange capacity of the membrane elements of the invention is described in EP-A-0 490 940.

Membranes containing polyamides derivatized with polymerizable double bonds, in accordance with DE-OS-195 01 726, are very well suited for the apparatus of the invention or for conducting the process of the invention.

The membrane module of the invention and the process of the invention can be used for numerous:applications for cleaning/separation of ligates from. a ligate-containing liquid as, for example, is generally known from the field of affinity chromatography. Affinity chromatography, in this case, is understood to be biospecific adsorption and also ion-exchange chromatography or metal-chelate chromatography.

Interesting applications relate to cleaning of monoclonal liquids, removal of proteases for stabilizing biological liquids, and recovering or therapeutically removing blood-plasma components from blood plasma or whole blood. For treatment of whole blood, for example, a hemodialyzer or hemodiafilter can be connected in series with, or directly coupled to, a membrane module of the invention. Substances normally eliminated in the urine are then removed in the usual way in the hemodialyzer or hemodiafilter. In the subsequent membrane module of the invention, in which whole blood is conducted in cross-flow mode through the first membrane elements, appropriately selected functional groups, immobilized in the module, can be used to selectively remove from the blood such substances as cytokines, albumin-bound toxins, or toxins in general with a molecular weight greater than about 10,000 D, i.e., substances that can be removed only inadequately by hemodialysis or hemodiafiltration.

Other applications include the removal of pyrogens from biological or pharmaceutical liquids, separation of enantiomers, isolation of enzymes, and cell selection by means of specific ligands that react with a particular surface protein of the cells, to mention only a few examples. The membrane modules of the invention are also very well suited to applications in the field of genetic engineering, if such applications require, for example, convective transport of genes to, for example, viruses or cells immobilized on and/or in the membrane.

In one embodiment, the membrane module of the invention can be used as a heparin adsorber for whole blood. In this case, the first membrane elements, through which the whole blood passes, serve preferably for plasma separation alone, and heparin adsorption occurs as substance-specific treatment via carrier materials immobilized in the outer space and/or in the second membrane elements. However, preferably heparin adsorption occurs only in the second membrane elements, which are provided with tentacles carrying DEA (diethylamino) groups as ligands. In this embodiment, the first and second membrane elements are preferably arranged with respect to one another such that the outer space is kept small. This delinking of plasma separation and heparin adsorption allows separate optimization of the membranes used for the respective membrane elements. This is also advantageous in that relatively inexpensive membranes can then be used for the plasma separation while the use of the membranes modified for heparin adsorption, which are relatively expensive due to the complex modification processes, is restricted to the second membrane elements.

As mentioned above, particles to be used as a matrix can be introduced into the outer space, around the first and second membrane elements, where particles are understood in the context of the present invention to include, for example, cells that react in a specific way with target substances directed toward them. In another embodiment, the membrane module of the invention can be used as an artificial organ, such as an artificial liver. In this case, animal hepatocytes, introduced via an opening in the housing, are introduced into and immobilized in the outer space around the first and second membrane elements. It is favorable in this case for the membrane-element arrangement to have a layered structure where the individual layers contain only first or only second membrane elements. It is also practical to introduce a nonwoven as a spacer between the layers, wherein the nonwoven can be designed such that it serves simultaneously as an anchoring point for the hepatocytes. In the application, the hepatocytes purify blood or blood plasma flowing through the first membrane elements in cross-flow mode, freeing it from products of metabolism and toxins. The hepatocytes are at the same time provided with oxygen and nutrients via the first membrane elements. The second membrane elements serve to retain the hepatocytes, while the plasma stream purified by the hepatocytes passes through these membrane elements. After passing out of the cavities of the second membrane elements, the purified plasma stream is combined with the blood or blood plasma passing out of the first membrane elements.

For applications in the area of enzymatic or generally catalytic treatment of liquids, hollow-fiber membranes can be selected on and/or in which enzymes or catalysts have been immobilized by methods that are known per se. For details of catalytic treatments that can be carried out using the membrane module of the invention or the process of the invention, the reader is referred to the European patent application EP-A-0 787 523, the relevant disclosures of which are expressly included herein as references.

The invention will now be explained in more detail with reference to the figures, which are simplified schematic representations:

FIG. 1: Membrane module with first and second membrane elements in the form of hollow-fiber membranes.

Figure 2:
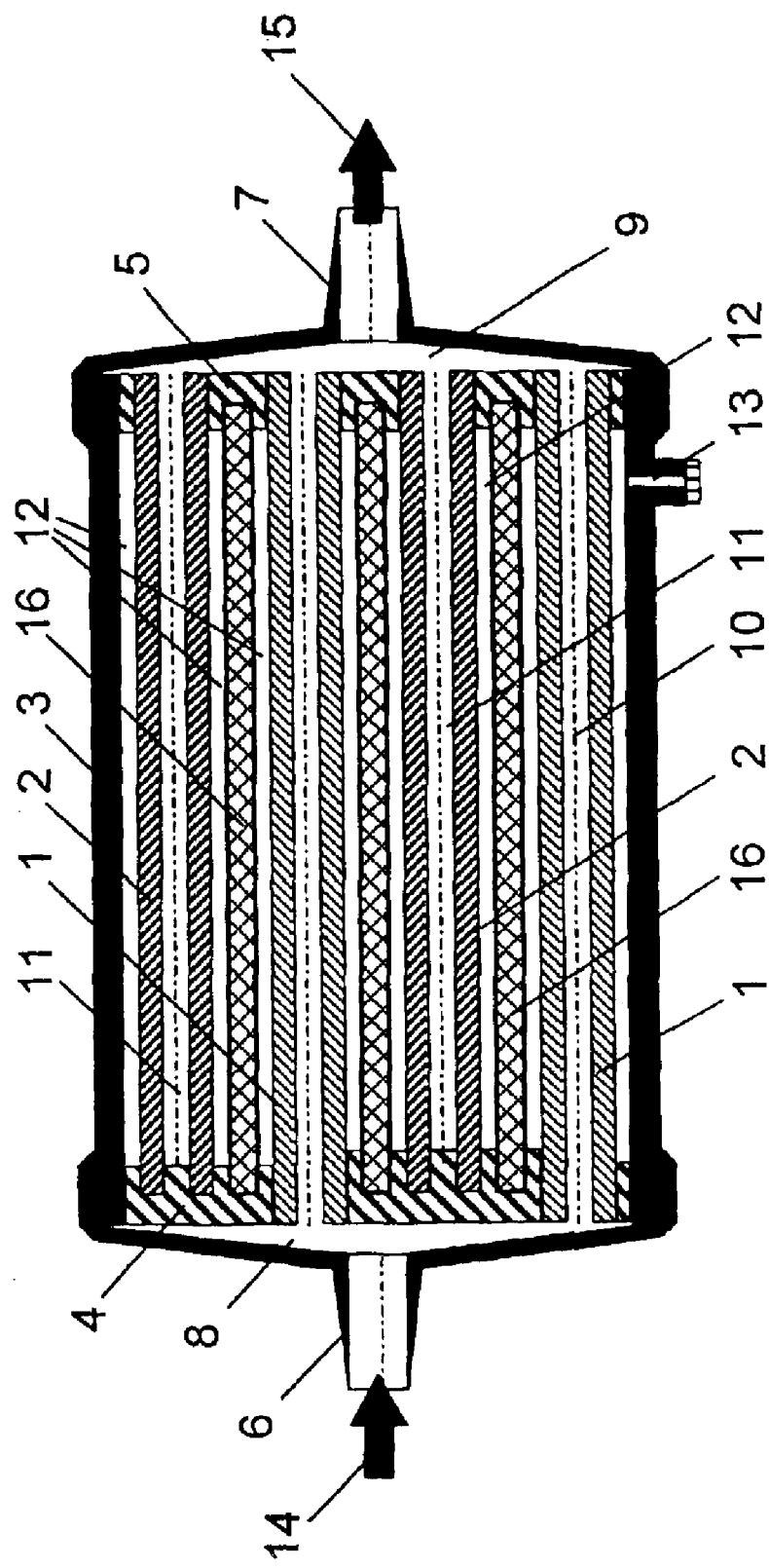
FIG. 2 is a membrane module with first and second membrane elements in the form of hollow-fiber membranes, wherein flat membranes are arranged in the outer space surrounding the membrane elements.

FIG. 2: Membrane module with first and second membrane elements in the form of hollow-fiber membranes, wherein flat membranes, are arranged in the outer space surrounding the membrane elements.

Figure 3:
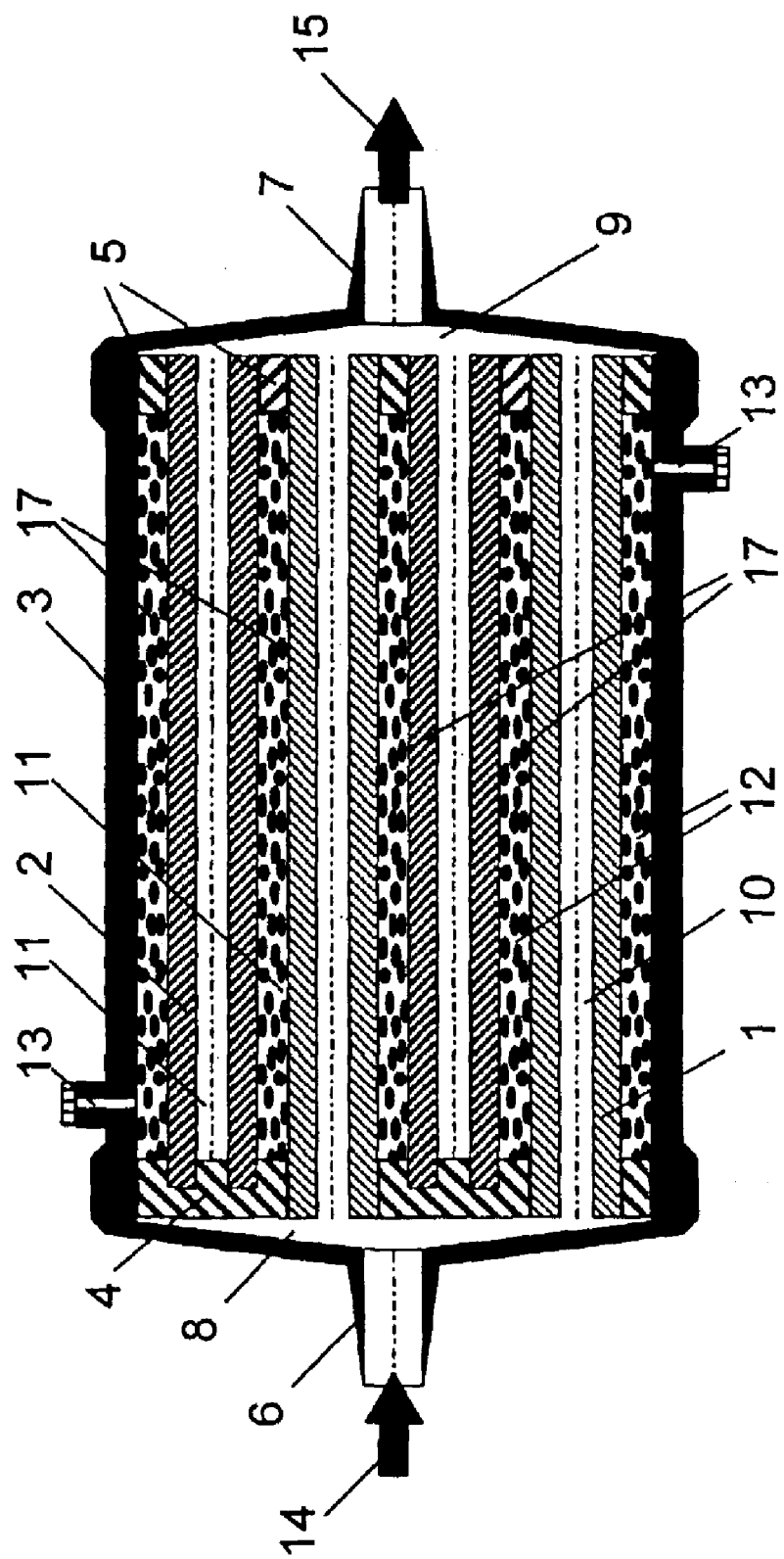
FIG. 3 is a membrane module with first and second membrane elements in the form of hollow-fiber membranes, where particles serving as carrier material are arranged in the outer space surrounding the membrane elements.

FIG. 3: Membrane module with first and second membrane elements in the form of hollow-fiber membranes, where particles serving as carrier material are arranged in the outer space surrounding the membrane elements.

Figure 4:
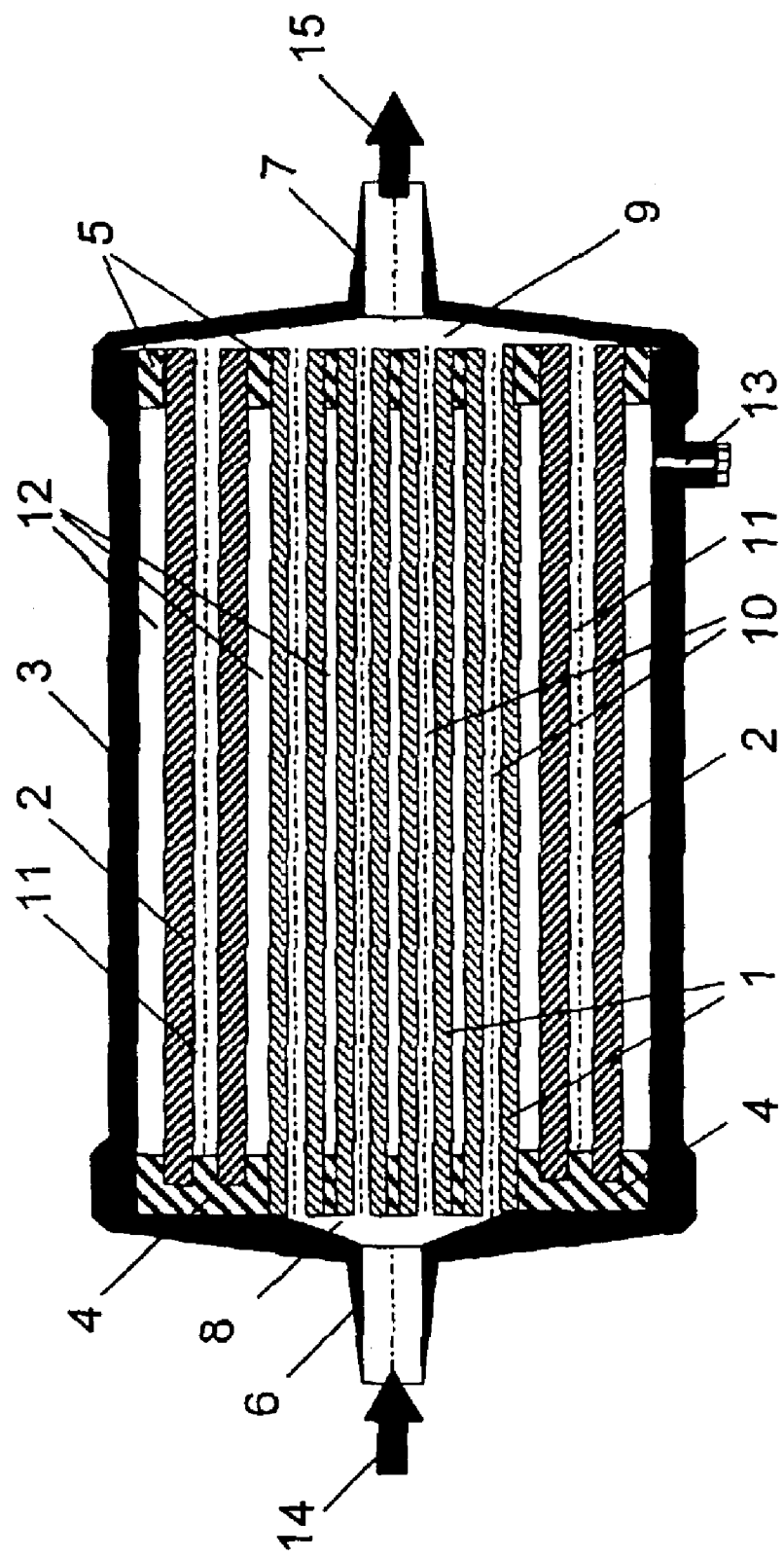
FIG. 4 is a membrane module with first and second membrane elements in the form of hollow-fiber membranes, in which the first membrane elements are collected together in the center of the module and the second membrane elements are arranged in the form of a ring surrounding the first membrane elements.

FIG. 4: Membrane module with first and second membrane elements in the form of hollow-fiber membranes, in which the first membrane elements are collected together in the center of the module and the second membrane elements are arranged in the form of a ring surrounding the first membrane elements.

Figure 5:
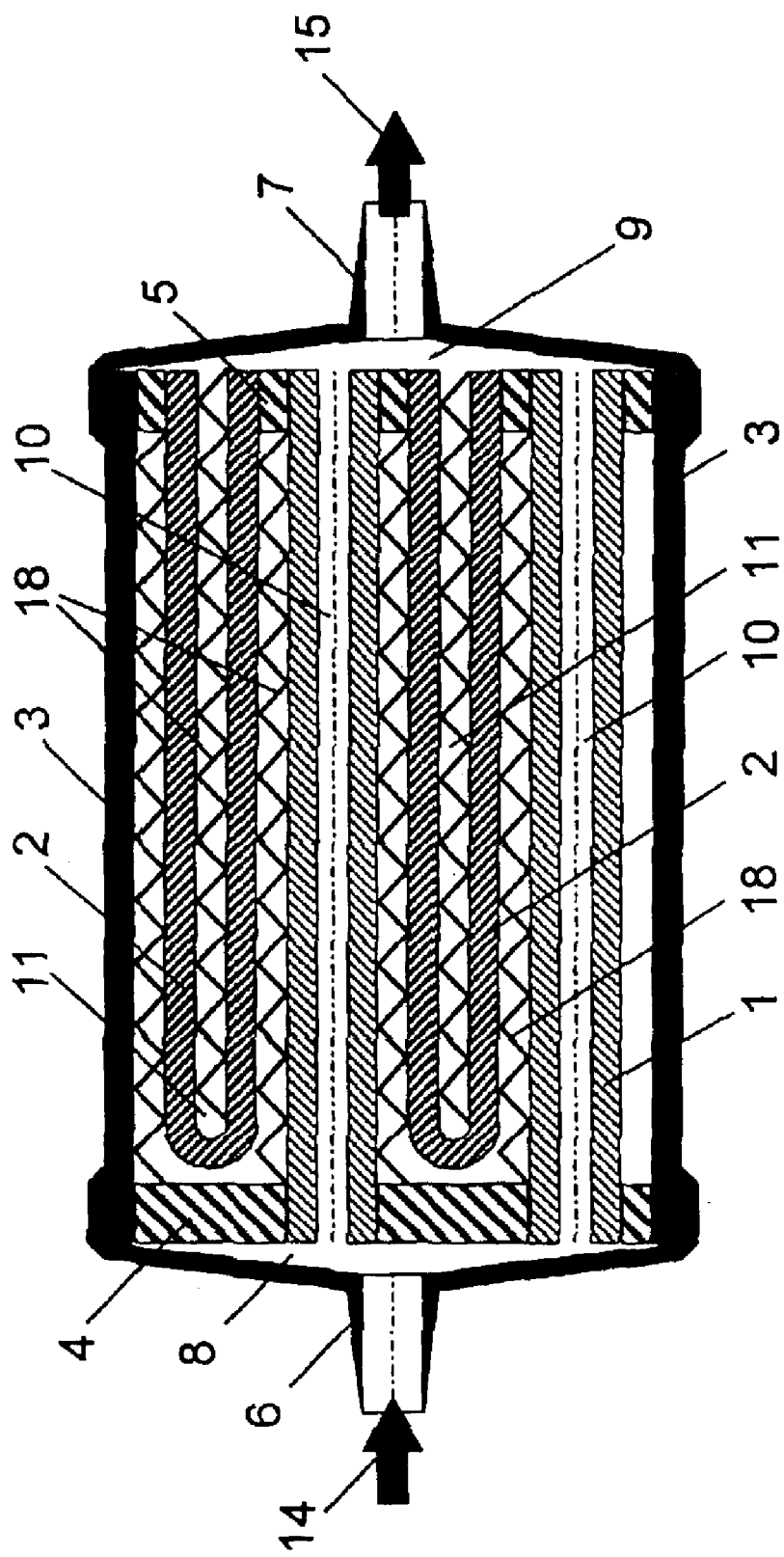
FIG. 5 is a membrane module in which the first membrane elements comprise hollow-fiber membranes and the second membrane elements comprise flat membranes folded in a U-shape.

FIG. 5: Membrane module in which the first membrane elements consist of hollow-fiber membranes and the second membrane elements of flat membranes folded in a U-shape.

Figure 6:
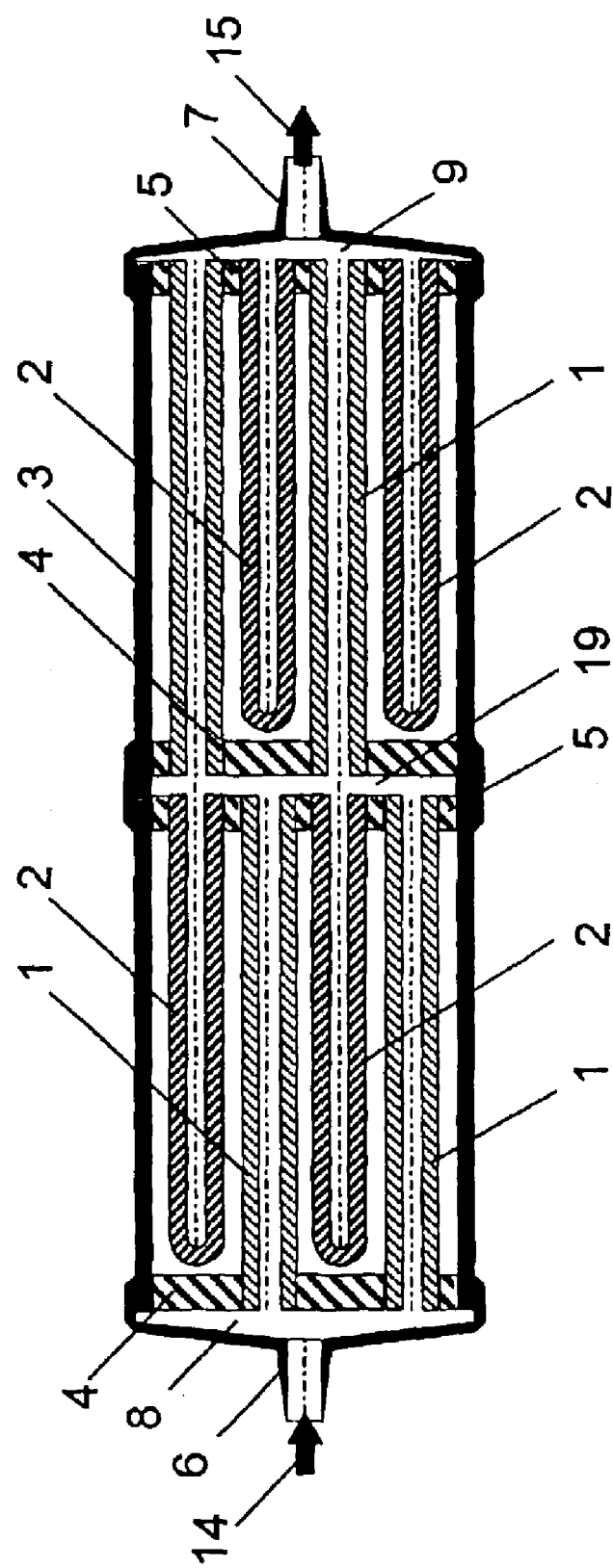
FIG. 6 is a membrane module with two module stages, in which the first membrane elements comprise hollow-fiber membranes and the second membrane elements comprise flat membranes folded in a U-shape.

FIG. 6: Membrane module with two module stages, in which the first membrane elements comprise hollow-fiber membranes and the second membrane elements of flat membranes folded in a U-shape.

FIG. 1 shows a longitudinal section through a membrane module of the invention with first membrane elements 1 and second membrane elements 2 in the form of hollow-fiber membranes embedded in sealing compounds 4, 5 in a housing 3. In the case shown, the hollow-fiber membranes are arranged in first layers, comprising only first membrane elements 1, and second layers, comprising only second membrane elements 2. The layers in this representation extend alongside the hollow-fiber membranes and are perpendicular to the plane of the drawing. The first and second layers are stacked in alternating sequence, as shown in FIG. 1.

Such an alternating sequence, as viewed in longitudinal section, of first membrane elements 1 and second membrane elements 2 can also be obtained if a hollow-fiber mat containing only first membrane elements 1 and another containing only second membrane elements 2 are superimposed and wound spirally. In such cases the housing 3 preferably has a round cross-section.

The housing 3 has an inlet arrangement 6 to feed the fluid to be treated into the housing 3 as well as an outlet arrangement 7 to remove the treated fluid from the housing 3. The inlet arrangement 6 is in communication with a distribution space 8, and the outlet arrangement 7 with a collection space 9. The first membrane elements 1 are embedded in the sealing compounds 4, 5 such that their ends extend through the sealing compounds 4, 5. The membrane elements are open at these ends, so that the cavities 10 of the first membrane elements 1 open into the distribution space 8 as well as the collection space 9. The second membrane elements 2 are embedded in the sealing compounds 4, 5 such that they are closed by sealing compound 4 at the end pointing toward the distribution space 8. At the end pointing toward the collection space 9, they extend through the sealing compound 5 and are open at this end. The cavities 11 of the second membrane elements 2 are thus open only at the end pointing toward the collection space 9.

In the example shown, the outer space 12 formed between the membrane elements 1, 2 and the sealing compounds 4, 5 can be filled or deaerated via a sealable opening 13.

In one embodiment of the process of the invention, the fluid to be treated, indicated by arrow 14, flows as a feed stream through the inlet arrangement 6 into the distribution space 8 of the membrane module as shown in FIG. 1, and then through the cavities 10 of the first membrane elements 1 in cross-flow mode. Part of the feed stream passes as a permeate through the porous walls of the first membrane elements 1 and into the outer space 12. The remaining part of the feed stream, the retentate, leaves the cavities 10 of the first membrane elements 1 at those ends of the first membrane elements 1 embedded in the sealing compound 5, and enters the collection space 9.

The permeate passes out of the outer space through the walls of the second membrane elements 2 and into their cavities 11, leaving the latter through the open ends embedded in sealing compound 5, to be combined with the retentate in the collection space 9. The fluid stream of combined permeate and retentate leaves the membrane module of the invention as treated fluid, indicated by arrow 15, via the outlet arrangement 7. The substance-specific treatment of the fluid to be treated takes place in the walls of the first membrane elements 1 and/or in the outer space 12 and/or in the walls of the second membrane elements 2.

FIG. 2 shows an embodiment of the membrane module of the invention in which flat membranes 16 are arranged in the outer space 12 surrounding the membrane elements 1, 2, and are embedded along with the membrane elements 1, 2, in the sealing compounds 4, 5. On its way from the first membrane elements 1 to the second membrane elements 2, therefore, the permeate passes through the flat membranes 16 in dead-end mode. As stated above, the flat membrane is preferably the carrier material and matrix for functional groups. However, it can also serve solely as a dead-end filtration stage and effect a fractionation on the basis of particle size.

In the case where the arrangement of first and second membrane elements 1, 2 is constructed from spirally wound hollow-fiber-mats, each comprising either only first membrane elements or only second membrane elements, the flat membrane 16 in the outer space is easily positioned by placing it between the hollow-fiber mats before spiral winding and then winding it together with the hollow-fiber mats. In applications where the hollow-fiber membranes 1, 2 must be spaced from the flat membrane 16, a flat spacer may be placed if necessary between the flat membrane 16 and the respective hollow-fiber mat, and wound along with them.

FIG. 3 shows an embodiment of a membrane module of the invention which is similar to that shown in FIG. 1, but in which particles 17, serving as the matrix for the functional groups, have been inserted as carrier material into the outer space 12 around the membrane elements 1, 2. In order to achieve a stable positioning of the particles, they may also be embedded in a nonwoven that serves simultaneously as a spacer between the layers of the first and second membrane elements 1, 2. The particles 17 may, for example, be filled through the openings 13 into the outer space 12 and distributed evenly in the outer space 12 by rotating the module or subjecting it to a tumbling motion.

As stated above, particles are understood to also include cells that interact in a specific manner with target substances directed toward them. In one embodiment, the membrane module of the invention can be used as an artificial organ, such as an artificial liver.

FIG. 4 shows another membrane module of the invention, whose membrane elements 1, 2 comprise hollow-fiber membranes. However, the membrane module of FIG. 4 contains a larger number of first membrane elements 1 for cross-flow filtration as compared with the number of second membrane elements 2 for dead-end filtration. In the case shown, the ratio $N_1/N_2$ of the number $N_1$ of first membrane elements 1 to the number $N_2$ of second membrane elements 2 is equal to 4, the first membrane elements 1 being collected together in the center of the module and the second membrane elements 2, possibly in the form of a hollow-fiber mat, being arranged in a ring around the bundle of the first membrane elements 1.

Different values of the ratio $N_1/N_2$ are generally possible, depending on the application of the membrane module of the invention, the ratio preferably lying in the range about 0.5 to about 10. In regard to the arrangement, several alternatives are possible. If the ratio $N_1/N_2$ is 4, for example, a stacked structure of the membrane-element arrangement might combine four layers of hollow-fiber mats having first membrane elements with one layer of a hollow-fiber mat having second membrane elements. However, hollow-fiber mats could also be produced that already have first and second membrane elements in the ratio 4:1.

An embodiment of the membrane module of the invention in which the second membrane elements are made from flat membranes is shown in FIG. 5. The module of FIG. 5 has an arrangement of first layers having first membrane elements 1 in the form of hollow-fiber membranes and second layers having second membrane elements 2 made of flat membranes folded in a U-shape. The cavity 11 of the second membrane elements is, as shown in the sectional representation, bounded by the flanks of the respective flat membrane formed by the U-shaped folding and by the edge of the U-shaped fold, and, as in the example shown in FIG. 5, stabilized by a spacer 18. Spacers 18 are also inserted at the same time between the first membrane elements 1 and the second membrane elements 2 to achieve stable positioning particularly of the second membrane elements 2 in the module housing 3.

The fold edges, which point toward the distribution space 8 and which in the present example are not embedded along with the corresponding ends of the first membrane elements 1 in sealing compound 4, close off, together with the side edges, which are also closed and are adjacent to the fold edge, the second membrane elements 2, made from flat membranes, from the outer space, so that the cavities of these elements are closed at the end pointing toward the distribution space 8. The permeate that has permeated through the walls of the first membrane elements thus passes through the second membrane elements 2 in dead-end mode in the application. The cavities 11 of the second membrane elements 2 are open in the direction of the collection space 9, so that the permeate can flow out of the cavities of the second membrane elements 2 into the collection space 9, where it is combined with the retentate flowing out of the cavities 10 of the first membrane elements 1.

FIG. 6 shows a membrane module of the invention comprising two membrane-element arrangements of first and second membrane elements 1, 2, as consecutively arranged module stages when viewed in the direction of flow through the housing 3. The structure of the individual arrangements corresponds to that of the arrangement shown in FIG. 5 comprising first and second membrane elements 1, 2 with hollow-fiber membranes as first membrane elements 1 and flat membranes folded in a U-shape as second membrane elements 2. The individual module stages are separated from each other, and the resulting space 19 allows free flow between the module stages, which is the collection space for the first module stage, referred to the direction of flow through the housing, positioned ahead of space 19 and in which the retentate and permeate from the first module stage are combined. The space 19 is at the same time the distribution space for the second module stage, referred to the direction of flow, positioned following space 19 and from which the fluid treated in the first module stage is distributed to the first membrane elements 1 of the second module stage. The retentate and permeate leaving the second module stage are combined in the collection space 9, and the fluid 15, having been treated in two module stages, is removed from the membrane module via the outlet arrangement 7.

What is claimed is:

1. Membrane module for substance-specific treatment of a fluid, comprising a housing, an inlet arrangement for feeding the fluid to be treated into a distribution space in the housing, an outlet arrangement for removing the treated fluid from the housing via a collection space, and first membrane elements arranged in the housing and having a first porous, semipermeable wall, each having one end pointing toward the distribution space and the other end toward the collection space and at least one or more first cavities formed by the first porous, semipermeable wall, wherein the first membrane elements are embedded in a first sealing compound at the end pointing toward the distribution space and in a second sealing compound at the end pointing toward the collection space, such that the ends extend through the first and second sealing compounds and each of the first cavities of the first membrane elements is open at the end pointing toward the distribution space as well as at the end pointing toward the collection space and opens into the distribution space and collection space, wherein the membrane module also comprises second membrane elements arranged in the housing and having a second porous, semipermeable wall, one end of the second membrane elements pointing toward the distribution space and the other end toward the collection space, and at least one or more second cavities formed by the second porous, semipermeable wall, wherein the second membrane elements, at the end pointing toward the collection space, are embedded, along with the first membrane elements, in the second sealing compound such that these ends extend through the second sealing compound, and each of the second cavities of the second membrane elements is open at this end and opens into the collection space, and the second membrane elements are closed at the end pointing toward the distribution space, the first and second membrane elements forming a membrane-element arrangement, and an outer space being formed between the sealing compounds that is partitioned in a fluid-tight manner from the distribution space and the collection space and delimited by the sealing compounds, the inner waif of the housing, and the membrane elements.

2. Membrane module according to claim 1, wherein the arrangement of the first membrane elements and the second membrane elements comprises sheet-form layers.

3. Membrane module according to claim 2, wherein the arrangement of the first membrane elements and the second membrane elements comprises planar sheet-form layers superimposed to form a stack.

4. Membrane module according to claim 2, wherein the arrangement of the first membrane elements and the second membrane elements comprises sheet-form layers wound spirally about a winding axis.

5. Membrane module according to claim 2, wherein the arrangement of the first membrane elements and the second membrane elements comprises first layers and second layers, the first layers comprising only first membrane elements and the second layers comprising only second membrane elements.

6. Membrane module according to claim 5, wherein the arrangement of the first membrane elements and the second membrane elements comprises an alternating sequence of first and second layers.

7. Membrane module according to claim 1, wherein the first membrane elements and second membrane elements are hollow-fiber membranes.

8. Membrane module according to claim 2, wherein the first membrane elements and second membrane elements are hollow-fiber membranes and the hollow-fiber membranes within the layers are arranged essentially parallel to one another.

9. Membrane module according to claim 7, wherein the hollow-fiber membranes are bound into at least one hollow-fiber mat.

10. Membrane module according to claim 9, wherein the hollow-fiber membranes are bound into the at least one hollow-fiber mat by means of textile threads.

11. Membrane module according to claim 9, wherein at least one hollow-fiber mat is folded zigzag fashion to form a stack that constitutes the arrangement of the first membrane elements and the second membrane elements.

12. Membrane module according to claim 1, wherein the first membrane elements are hollow-fiber membranes and the second membrane elements comprise at least one flat membrane.

13. Membrane module according to claim 12, wherein the second membrane elements comprise an essentially rectangular or square flat membrane folded into a U-shape, wherein, in addition to a fold edge, two other side edges are closed, flanks formed by folding the flat membrane into a U-shape are spaced to form the at least one or more second cavities, and a remaining, open side edge points toward the collection space.

14. Membrane module according to claim 12, wherein the second membrane elements comprise two flat membranes essentially parallel to each other and essentially rectangular or square, arranged such that edges of the two flat membranes run parallel to each other, wherein the flat membranes are spaced from each other and are positively joined to each other at the edge pointing toward the distribution space and the edges perpendicular thereto, a remaining, open side edge pointing toward the collection space.

15. Membrane module according to claim 1, wherein the housing comprises a matrix on and/or in which functional groups are immobilized.

16. Membrane module according to claim 15, wherein a matrix for the functional groups comprises the first and/or second membrane elements.

17. Membrane module according to claim 15, wherein a matrix for the functional groups comprises fluid-permeable carrier materials introduced between the first and second membrane elements.

18. Membrane module according to claim 17, wherein the carrier materials are semipermeable, porous flat membranes.

19. Membrane module according to claim 17, wherein the carrier materials are particles.

20. Membrane modules according to claim 17, wherein the matrix comprises different functional groups.

21. Membrane module according to claim 1, wherein, in a direction of the extent of the housing, between the inlet arrangement and the outlet arrangement of the membrane module, a plurality of arrangements of the first membrane elements and the second membrane elements are arranged sequentially as stages.

22. Process for substance-specific treatment of a fluid, comprising at least the following steps:
  a) introducing the fluid to be treated as a feed stream into a module comprising a housing, an inlet arrangement for feeding the fluid to be treated into a distribution space in the housing, an outlet arrangement for removing the treated fluid from the housing via a collection space, and first membrane elements arranged in the housing and having a first porous, semipermeable wall, each having one end pointing toward the distribution space and the other end toward the collection space and at least one or more first cavities formed by the first porous, semipermeable wall, wherein the first membrane elements are embedded in a first sealing compound at the end pointing toward the distribution space and in a second sealing compound at the end pointing toward the collection space, such that the ends extend through the first and second sealing compounds and each of the first cavities of the first membrane elements is open at the end pointing toward the distribution space as well as at the end pointing toward the collection space and opens into the distribution space and collection space, wherein the module also comprises second membrane elements arranged in the housing and having a second porous, semipermeable wall, one end of the second membrane elements pointing toward the distribution space and the other end toward the collection space, and at least one or more second cavities formed by the second porous, semipermeable wall, wherein the second membrane elements, at the end pointing toward the collection space, are embedded, along with the first membrane elements, in the second sealing compound such that these ends extend through the second sealing compound, and each of the second cavities of the second membrane elements is open at this end and opens into the collection space, and the second membrane elements are closed at the end pointing toward the distribution space, the first and second membrane elements forming a membrane-element arrangement, and an outer space being formed between the sealing compounds that is partitioned in a fluid-tight manner from the distribution space and the collection space and delimited by the sealing compounds, the inner wall of the housing, and the membrane elements.
  b) directing the feed stream in cross-flow mode along one side of the first membrane elements such that part of the feed stream passes as a permeate through the first membrane elements and exits from the first membrane elements on its other side, while a remainder of the feed stream continues flowing along the one side of the first membrane elements as a retentate,
  c) introducing at least a substantial portion of the permeate in dead-end mode to the second membrane elements on one side of the second membrane elements, passing of the permeate through the second membrane elements, and removing it from the second membrane elements on its other side,
  d) combining the permeate and the retentate within the module to yield a treated fluid, and
  e) removing the treated fluid from the module;
  wherein the permeate is subjected to at least one substance-specific treatment between separation from the feed stream and recombination with the retentate.

23. Process according to claim 22, wherein steps b) to d) are conducted multiple times.

24. Process according to claim 22, wherein the treatment of the fluid is carried out in a plurality of arrangements of the first membrane elements and the second membrane elements arranged sequentially as stages in the direction of the extent of the housing between the inlet arrangement and the outlet arrangement of the membrane module.

25. Process according to claim 24, wherein the treatment is carried out in up to 10 stages.

26. Process according to claim 22, wherein the fluid to be treated is recirculated.

27. Process according to claim 22, wherein the fluid to be treated is a suspension.

28. Process according to claim 22, wherein the permeate, between separation from the feed stream and recombination with the retentate, passes through a matrix on and/or in which functional groups suitable for the substance-specific treatment have been immobilized.

29. Process according to claim to claim 28 for cleaning/separation of ligates from a ligate-containing liquid by affinity, wherein the matrix is selected on and/or in which ligands for the ligates are immobilized.

30. Process according to claim 28 for catalytic treatment of fluids, wherein the matrix is selected on and/or in which catalysts are immobilized.

31. Membrane module according to claim 8, wherein the hollow-fiber membranes are bound into at least one hollow-fiber mat.

32. Membrane module according to claim 7, wherein the hollow-fiber membranes have a wall thickness between about 15 $\mu$m and about 900 $\mu$m.

33. Membrane module according to claim 32, wherein the wall thickness for the first membrane elements is between about 30 $\mu$m and about 100 $\mu$m, and the wall thickness for the second membrane elements is between about 100 $\mu$m and about 300 $\mu$m.

34. Membrane module according to claim 7, wherein the hollow-fiber membranes have a lumen hydraulic diameter of about 50 $\mu$m to about 1500 $\mu$m.

35. Membrane module according to claim 1, wherein the first and second membrane elements have a mean porosity between about 50% and about 90% by volume.

36. Membrane module according to claim 1, wherein the first and second membrane elements have a mean pore diameter between about 0.01 $\mu$m and about 10 $\mu$m.

37. Membrane module according to claim 15, wherein the matrix has a mean pore diameter between about 0.2 $\mu$m and about 10 $\mu$m.

* * * * *

UNITED STATES PATENT AND TRADEMARK OFFICE
CERTIFICATE OF CORRECTION

PATENT NO. : 6,866,783 B2
DATED : March 15, 2005
INVENTOR(S) : Ulrich Baurmeister et al.

It is certified that error appears in the above-identified patent and that said Letters Patent is hereby corrected as shown below:

Column 9,
Line 62, delete ";".

Column 16,
Line 64, delete "su".

Column 18,
Line 66, delete ":".

Column 21,
Line 64, "hollow-fiber-mats" should be -- hollow-fiber mats --.

Column 24,
Line 14, "waif" shoulde be -- -wall --.

Signed and Sealed this

Fourteenth Day of June, 2005

JON W. DUDAS
*Director of the United States Patent and Trademark Office*